US011197974B2

(12) United States Patent
Kremer et al.

(10) Patent No.: US 11,197,974 B2
(45) Date of Patent: Dec. 14, 2021

(54) ENTRAINING RESPIRATION

(71) Applicant: BOSE CORPORATION, Framingham, MA (US)

(72) Inventors: Kathleen E. Kremer, Westborough, MA (US); Steven Carl Pletcher, Hopkinton, MA (US); Matthew Carpenter, North Attleboro, MA (US); Danielle Hicks, Boston, MA (US); Marc Labbe, Arlington, MA (US); Brian David Mulcahey, Sudbury, MA (US)

(73) Assignee: BOSE CORPORATION, Framingham, MA (US)

( * ) Notice: Subject to any disclaimer, the term of this patent is extended or adjusted under 35 U.S.C. 154(b) by 33 days.

(21) Appl. No.: 16/045,980

(22) Filed: Jul. 26, 2018

(65) Prior Publication Data
US 2019/0030278 A1    Jan. 31, 2019

Related U.S. Application Data

(60) Provisional application No. 62/537,132, filed on Jul. 26, 2017.

(51) Int. Cl.
*A61M 21/02* (2006.01)
*A61B 5/08* (2006.01)
(Continued)

(52) U.S. Cl.
CPC ............ *A61M 21/02* (2013.01); *A61B 5/0816* (2013.01); *A61B 5/486* (2013.01); *A61B 5/4812* (2013.01);
(Continued)

(58) Field of Classification Search
CPC ............... A61M 21/00; A61M 21/02; A61M 2021/0027; A61M 2021/0088; A61B 5/0816; A61B 5/4812
See application file for complete search history.

(56) References Cited

U.S. PATENT DOCUMENTS

| 5,167,610 A | 12/1992 | Kitado et al. |
| 6,819,957 B1 * | 11/2004 | Le ..................... A61N 1/0452 128/905 |

(Continued)

FOREIGN PATENT DOCUMENTS

WO    2010070569 A1    6/2010

OTHER PUBLICATIONS

International Search Report and Written Opinion from corresponding International Application No. PCT/US2018/043837 dated Sep. 21, 2018.

*Primary Examiner* — Carrie R Dorna
(74) *Attorney, Agent, or Firm* — Lando & Anastasi, LLP (57) ABSTRACT

Systems and methods are provided that provide respiration entrainment cues to a user to encourage relaxation or a sleep state. The entrainment cues may be audible, visible, or tactile (or any combination). The entrainment cues include a rhythmic component associated with a target respiration rate and may include sub-components associated with a target breath architecture, such as an inhale-exhale cycle. The systems and methods detect the user's respiration to determine whether the user's respiration matches the entrainment cues or whether the user has fallen asleep.

22 Claims, 2 Drawing Sheets

(51) Int. Cl.
*A61M 21/00* (2006.01)
*A61B 5/00* (2006.01)
*A61B 7/00* (2006.01)
*A61B 5/18* (2006.01)

(52) U.S. Cl.
CPC ............... *A61B 7/003* (2013.01); *A61B 5/18* (2013.01); *A61B 5/4806* (2013.01); *A61B 5/7405* (2013.01); *A61B 2560/0242* (2013.01); *A61M 2021/0027* (2013.01); *A61M 2021/0044* (2013.01); *A61M 2021/0088* (2013.01); *A61M 2230/40* (2013.01); *A61M 2230/42* (2013.01)

(56) References Cited

U.S. PATENT DOCUMENTS

| | | | |
|---|---|---|---|
| 7,041,049 B1* | 5/2006 | Raniere | A61M 21/02 |
| | | | 128/905 |
| 8,454,491 B2 | 6/2013 | Schmeink et al. | |
| 2010/0240945 A1 | 9/2010 | Bikko | |
| 2015/0080642 A1* | 3/2015 | Fox | A61M 21/00 |
| | | | 600/26 |
| 2015/0367097 A1 | 12/2015 | Gavish | |
| 2016/0151603 A1* | 6/2016 | Shouldice | H04R 3/00 |
| | | | 600/28 |

* cited by examiner

ENTRAINING RESPIRATION

CROSS-REFERENCE TO RELATED APPLICATIONS

This application claims the benefit under 35 U.S.C. § 119(e) of U.S. Provisional Patent Application No. 62/537,132 titled ENTRAINING RESPIRATION THROUGH AUDIO and filed on Jul. 26, 2017.

This application further relates to U.S. patent application Ser. No. 15/267,567 titled SLEEP ASSISTANCE DEVICE and to U.S. patent application Ser. No. 15/267,848 titled SLEEP SYSTEM, each of which was filed on Sep. 16, 2016 and is herein incorporated by reference in its entirety for all purposes.

TECHNICAL FIELD

This disclosure relates to providing cues to entrain (e.g., guide) a user's respiration rate and/or breath architecture (e.g., inhale/exhale cycle) to encourage relaxation, meditation, a sleep state, or the like.

BACKGROUND

A significant number of people report having trouble falling asleep at night. Additionally, some people need to sleep at differing periods (e.g., night shift workers) and may have trouble getting to sleep. Minds racing, undesired thoughts, restlessness, adrenaline, and other factors may affect a person's ability to relax or fall asleep. A focus on controlled breathing at a reduced respiration rate may assist many people in falling asleep more quickly or more reliably.

SUMMARY

Aspects and examples are directed to systems and methods that produce user-discernible cues (such as audio sounds, visible indicators, or haptic cues) having a rhythmic component to which a user is intended to match his or her breathing, by respiration rate and/or architecture. The cue is an entrainment cue and the systems and methods may monitor the user's respiration rate or breathing architecture (or both) to determine whether the user has successfully matched the entrainment cue or has fallen asleep. If the user matches the entrainment cue (e.g., to within a threshold), the systems and methods may slow the rhythmic component to establish a new target respiration rate. If the user falls asleep, the systems and methods may stop providing the entrainment cue, and the systems and methods may transition to masking sounds, soothing sounds, or no sounds. In some examples, the systems and methods may transition entrainment cues, such as by reducing volume, altering equalization, mixing with other sounds, and/or in other ways intended to cause the user to reduce focus on the entrainment cue, prior to the user being detected as having fallen asleep. For example, systems and methods may begin transitioning entrainment cues at each step of reducing a target respiration rate, or after a certain target respiration rate has been established for a period of time. Such transitions may assist in encouraging sleep onset in various examples, e.g., by reducing focus on the entrainment cues as a sleep session approaches sleep onset.

In some examples, the systems and methods may provide entrainment cues when sleep is not a goal, such as for relaxation or for practice or training the user to match the entrainment cues. Certain systems and methods may provide entrainment cues to maintain a respiration rate and/or breath architecture, rather than to progressively alter or reduce respiration. In various examples, the systems and methods may adjust a target respiration rate to a higher rate. Various systems and methods may detect that a user hasn't fallen asleep, or has awoken, or has gotten up and returned to bed, for example, and may establish a target respiration rate and/or breath architecture based upon an earlier target, e.g., a higher respiration rate, and/or to re-initiate an entrainment session from the start.

According to one aspect, a system is provided that includes an input configured to be coupled to a biometric sensor, to receive information about respiration of a user from the biometric sensor, an output configured to be coupled to a transducer, to provide signals to control the transducer, and a processor coupled to the input and the output and configured to cause the transducer to provide entrainment cues having a rhythmic component at a target respiration character, determine a respiration parameter of the user, based at least in part upon the information from the biometric sensor, and adjust the entrainment cues responsive to determining that the user's respiration parameter meets a criterion.

Some examples include the biometric sensor coupled to the input. Certain examples include the transducer coupled to the output. In various examples, the transducer includes at least one of an acoustic transducer (e.g., a loudspeaker), a light, a light display, or a haptic transducer.

According to various examples, the entrainment cues may include any of audible indications (e.g., sounds), visible indications, tactile (e.g., haptic) indications, or any combination of these.

In some examples, the target respiration character includes at least one of a target respiration rate or a target breath architecture.

In various examples, the user's respiration parameter is one of a respiration rate or a breath architecture.

According to various examples, the criterion is a sleep criterion. In some examples, the sleep criterion may be based upon a variance of the user's respiration rate from a target respiration rate and may depend upon whether the variance meets a threshold. In certain examples, the processor is configured to adjust the entrainment cues by ceasing the entrainment cues responsive to determining that the user's respiration parameter meets the sleep criterion. In some examples, the processor may be configured to adjust the entrainment cues by reducing or fading the entrainment cues.

In certain examples, the processor is further configured to detect a waking criterion and to cause the transducer to provide the entrainment cues responsive to detecting the waking criterion.

According to some examples, the processor is further configured to detect a sleep stage transition and to cause the transducer to provide an output responsive to the sleep stage transition.

In various examples, the criterion is a matching criterion, e.g., upon which it is determined that the user's respiration "matches" one or more aspects of the target respiration character. The matching criterion may be based upon a variance of the user's respiration rate from a target respiration rate and may depend upon whether the variance meets a threshold. In certain examples, the processor is configured to adjust the entrainment cues by adjusting the target respiration character responsive to determining that the user's respiration parameter meets the matching criterion. In some examples, the processor may be configured to adjust the entrainment cues by gradually transitioning to the adjusted respiration character.

In some examples, the user's respiration parameter is a user's breath architecture and the processor is configured to adjust the entrainment cues by adjusting a breath architecture of the target respiration character. In certain examples the adjusted breath architecture of the target respiration character may match the user's breath architecture. In certain examples the adjusted breath architecture of the target respiration character falls between the user's breath architecture and the unadjusted breath architecture of the target respiration character.

In various examples, the processor is configured to determine that the user's respiration rate meets a sleep criterion based upon a variance of the user's respiration rate deviating from the target respiration rate by a threshold.

In various examples, a target respiration rate is within a range of five to nine respirations per minute.

In certain examples, a target respiration rate is a first target respiration rate and the processor is further configured to adjust the rhythmic component to a second target respiration rate responsive to detecting that the user's respiration rate matches the first target respiration rate. The processor may be configured to detect that the user's respiration rate matches the first target respiration rate based upon a variance of the user's respiration rate being within a threshold of the first target respiration rate. The processor may be configured to limit either of the first target respiration rate or the second target respiration rate to a lowest target respiration rate, the lowest target respiration rate being a target respiration rate beyond which the processor will not adjust the rhythmic component to be lower. In certain examples, a lowest target respiration rate may be within a range of 5.5 respirations per minute to 6.5 respirations per minute.

According to another aspect, a method of encouraging relaxation in a user is provided. The method includes producing entrainment cues having a rhythmic component of a target respiration character, detecting a respiration parameter of the user, determining whether the respiration parameter meets a criterion, and adjusting the entrainment cues responsive to determining that the respiration parameter meets the criterion.

In some examples, the target respiration character includes at least one of a target respiration rate or a target breath architecture.

In various examples, the user's respiration parameter is one of a respiration rate or a breath architecture.

In various examples, the criterion is a sleep criterion and adjusting the entrainment cues comprises ceasing the entrainment cues. In certain examples, determining whether the user's respiration parameter meets the sleep criterion comprises determining that a variance of the user's respiration rate deviates from a target respiration rate by a threshold. The target respiration rate may be within a range of five to nine respirations per minute.

In some examples, the criterion is a matching criterion that indicates the user's respiration matches the target respiration character and adjusting the entrainment cues comprises lowering a target respiration rate. In certain examples, determining that the user's respiration matches the target respiration character is based upon a variance of the user's respiration rate being within a threshold of the target respiration rate. The method may limit the target respiration rate to a lowest target respiration rate beyond which the target respiration rate is not lowered, in some examples. The lowest target respiration rate may be within a range of 5.5 respirations per minute to 6.5 respirations per minute.

According to another aspect, an apparatus is provided that includes a sensor configured to detect respiration of a user and a processor coupled to the sensor and having an output configured to be coupled to a loudspeaker, the processor being configured to cause the loudspeaker to play entrainment sounds having a rhythmic component at a first target respiration rate, determine a respiration rate of the user, based at least in part upon the sensor, and adjust the rhythmic component responsive to determining that the user's respiration rate meets a criterion.

In some examples, the processor is configured to adjust the rhythmic component to a second target respiration rate responsive to determining that the user's respiration rate matches the first target respiration rate.

In certain examples, the processor is configured to determine that the user's respiration rate matches the first target respiration rate based upon a variance of the user's respiration rate being within a threshold of the first target respiration rate.

In various examples, the processor is further configured to limit either of the first target respiration rate or the second target respiration rate to a lowest target respiration rate, the lowest target respiration rate being a target respiration rate beyond which the processor will not adjust the rhythmic component to be lower. In certain examples, the lowest target respiration rate may be within a range of 5.5 respirations per minute to 6.5 respirations per minute.

In some examples, the processor is configured to adjust the rhythmic component by causing the loudspeaker to cease playing entrainment sounds responsive to determining that the user's respiration rate meets a sleep criterion.

In certain examples, the processor is configured to detect that the user's respiration rate meets the sleep criterion based upon a variance of the user's respiration rate deviating from the target respiration rate by a threshold.

According to another aspect, a non-transitory computer readable medium is provided having encoded instructions that, when executed by a processor, cause the processor to receive signals from a sensor configured to detect respiration of a user, provide signals to a transducer to cause the transducer to produce entrainment cues having a rhythmic component with a target respiration character, determine a respiration parameter of the user based at least in part upon the signals from the sensor, and adjust the rhythmic component responsive to determining that the user's respiration parameter meets a criterion.

In various examples, the transducer includes at least one of an acoustic transducer (e.g., a loudspeaker), a light, a light display, or a haptic transducer.

According to various examples, the entrainment cues may include any of audible indications (e.g., sounds), visible indications, tactile (e.g., haptic) indications, or any combination of these.

In some examples, the target respiration character includes at least one of a target respiration rate or a target breath architecture.

In various examples, the user's respiration parameter is one of a respiration rate or a breath architecture.

According to various examples, the criterion is a sleep criterion. In some examples, the sleep criterion may be based upon a variance of the user's respiration rate from a target respiration rate and may depend upon whether the variance meets a threshold. In certain examples, the instructions cause the processor to adjust the entrainment cues by ceasing the entrainment cues responsive to determining that the user's respiration parameter meets the sleep criterion. In some examples, the instructions may be configured to cause the processor to adjust the entrainment cues by reducing or fading the entrainment cues.

In certain examples, the instructions may be configured to cause the processor to detect a waking criterion and to cause the transducer to provide the entrainment cues responsive to detecting the waking criterion.

According to some examples, the instructions may be configured to cause the processor to detect a sleep stage transition and to cause the transducer to provide an output responsive to the sleep stage transition.

In various examples, the criterion is a matching criterion, e.g., upon which it is determined that the user's respiration "matches" one or more aspects of the target respiration character. The matching criterion may be based upon a variance of the user's respiration rate from a target respiration rate and may depend upon whether the variance meets a threshold. In certain examples, the instructions may be configured to cause the processor to adjust the entrainment cues by adjusting the target respiration character responsive to determining that the user's respiration parameter meets the matching criterion. In some examples, the instructions may be configured to cause the processor to adjust the entrainment cues by gradually transitioning to the adjusted respiration character.

In some examples, the user's respiration parameter is a user's breath architecture and the instructions may be configured to cause the processor to adjust the entrainment cues by adjusting a breath architecture of the target respiration character. In certain examples the adjusted breath architecture of the target respiration character may match the user's breath architecture. In certain examples the adjusted breath architecture of the target respiration character falls between the user's breath architecture and the unadjusted breath architecture of the target respiration character.

In various examples, the instructions may be configured to cause the processor to determine that the user's respiration rate meets a sleep criterion based upon a variance of the user's respiration rate deviating from the target respiration rate by a threshold.

In various examples, a target respiration rate is within a range of five to nine respirations per minute.

In certain examples, a target respiration rate is a first target respiration rate and the instructions may be configured to cause the processor to adjust the rhythmic component to a second target respiration rate responsive to detecting that the user's respiration rate matches the first target respiration rate. The instructions may be configured to cause the processor to detect that the user's respiration rate matches the first target respiration rate based upon a variance of the user's respiration rate being within a threshold of the first target respiration rate. The instructions may be configured to cause the processor to limit either of the first target respiration rate or the second target respiration rate to a lowest target respiration rate, the lowest target respiration rate being a target respiration rate beyond which the processor will not adjust the rhythmic component to be lower. In certain examples, a lowest target respiration rate may be within a range of 5.5 respirations per minute to 6.5 respirations per minute.

Still other aspects, examples, and advantages of these exemplary aspects and examples are discussed in detail below. Examples disclosed herein may be combined with other examples in any manner consistent with at least one of the principles disclosed herein, and references to "an example," "some examples," "an alternate example," "vari- ous examples," "one example" or the like are not necessarily mutually exclusive and are intended to indicate that a particular feature, structure, or characteristic described may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide illustration and a further understanding of the various aspects and examples, and are incorporated in and constitute a part of this specification, but are not intended as a definition of the limits of the inventions. In the figures, identical or nearly identical components illustrated in various figures may be represented by a like numeral. For purposes of clarity, not every component may be labeled in every figure. In the figures.

DETAILED DESCRIPTION

Aspects of the present disclosure are directed to systems and methods that encourage relaxation or sleep onset by providing entrainment cues having rhythmic components to which a user is intended to match their breathing, thus encouraging respiration rate and/or breath architecture to promote relaxation or early sleep onset.

Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure, or characteristic described may be included in at least one example. The appearances of such terms herein are not necessarily all referring to the same example.

It is to be appreciated that examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, right and left, top and bottom, upper and lower, and vertical and horizontal are intended for convenience of description, not to limit the present systems and methods or their components to any one positional or spatial orientation.

Figure 1:
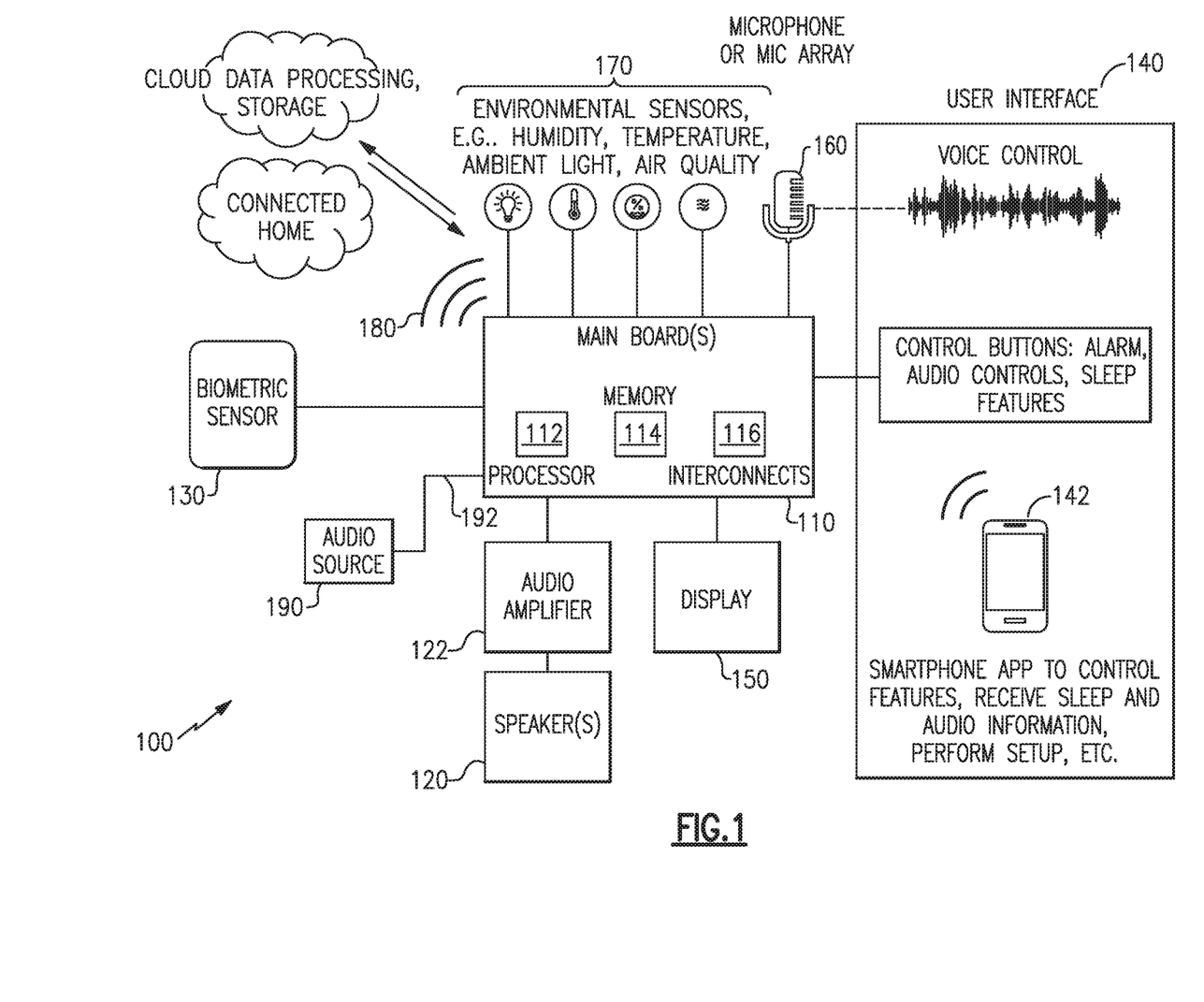
FIG. 1 is a schematic block diagram of an example system.

FIG. 1 illustrates an example system 100 in accord with aspects and examples described herein. The system 100 includes a processing unit 110, which includes a processor 112, memory 114, and various interconnects 116. The processing unit 110 may be coupled to various other components, such as audio output components that may include a speaker 120 (e.g., an acoustic driver), which may further be a number of speakers, that may be driven by one or more amplifier(s) 122, for example. In some examples, the speaker 120 may be a remote speaker to which audio signals may be provided via a network connection and/or may be controllable via the network connection. Alternatively or additionally, the system 100 may include one or more interfaces to which a speaker 120 may be coupled, such as an audio line out connector, speaker terminal, wireless interface (e.g., BLUETOOTH® wireless technology), etc. Some examples may not use audio for entrainment cues and therefore may not include a speaker 120 or speaker output.

The memory 114 may store various program instructions, user data, audio sound files, and the like. In various examples, the system 100 may include a user interface 140, which may include control buttons, knobs, touchscreens, and the like. The system 100 may include a display 150 for displaying various information to a user, such as date and time information (e.g., an alarm clock), sleep history (e.g., from a sleep log stored in the memory 114), weather, traffic, etc. The display 150 may be integrated with a touchscreen, as part of the user interface 140, in some examples.

The system 100 may be incorporated into any of numerous form factors of physical devices or audio systems. For example, the system 100 may be incorporated into a tabletop loudspeaker, such as for use on a bedside table, e.g., an "alarm clock." In other examples, the system 100 may be incorporated into headphones, a headset, earbuds, or other personal wearable form factors. In yet other examples, various components may be interconnected to form the system 100, such as a home audio system interconnected with a remote (e.g., wired or wireless) entrainment module (e.g., a housing including the core processing unit 110) and/or a biometric sensor 130 (discussed in greater detail below). In various examples, the processing unit 110 may be coupled into a housing with, or be remote from, the speaker 120, the user interface 140, and/or the biometric sensor 130. In certain examples, a speaker 120 and a biometric sensor 130 are affixed to or incorporated with an earbud form factor for wearing in relative proximity to the ear canal and/or partially or fully inserted into an ear canal. Various examples may include a sleep mask or other wearable component. Various examples may provide entrainment cues by visible means (e.g., light components, displays, etc.), haptic (e.g., vibration, tactile) means, audible means, or any combination of these. In some examples, entrainment cues may be provided via a handheld device, such as by haptic, audible, or visual cues provided through a smartphone or via a smartphone application. In some examples, a device (such as a smartphone) may be placed or worn on the user's chest and may detect user respiration via microphone, accelerometer, and/or other means, and may provide entrainment cues by sound, vibration, and/or other means. In other examples, a device incorporating systems and methods described herein may be worn about the head or eyes or elsewhere on the user's body. In some examples, a device incorporating systems and methods described herein may be incorporated with, attached to, or placed under or around various bedding, e.g., pillows, sheets, mattress, etc.

In various examples, the processing unit 110 may provide audio signals to the speaker 120 to play sounds having a rhythmic component, the rhythmic component is intended to cause (or assist) a user to adopt a respiration rate that matches the rhythmic component. Accordingly, the audio signals (or soundtrack) may be intended to induce a target respiration and/or a target breath architecture (e.g., inhale/exhale ratio, with a hold component in some examples) by a user, which may help induce relaxation, drowsiness, and/or various sleep states. Portions of an audio signal that include such a rhythmic component are referred to herein as entrainment sounds. In some examples, the system 100 may provide instructions (e.g., visible or audible) to a user that he/she should actively try to match his/her respiration rate to the entrainment sounds. In other examples, the system 100 may produce the entrainment sounds without instruction. A user may intentionally match their respiration rate and/or breath architecture (e.g., due to prior instruction or experience), or may subliminally tend to match their respiration rate or breath architecture to the entrainment sounds. Active effort to match the entrainment sounds, by a user who has learned or been instructed to do so, may be more effective at inducing a sleep state. As used herein, the term "respiration character" may include any of respiration rate, breath architecture, or both, and various examples may operate to optimize one or the other, or both, to encourage sleep, relaxation, meditation, etc.

In some examples, the system 100 produces entrainment sounds including a rhythmic component associated with a target respiration rate. In some examples, the target respiration rate may be a fixed respiration rate. In some examples, the system 100 adjusts the entrainment sounds to reduce a target respiration rate over time. In various examples, a lowest target respiration rate may be in a range of 5 to 9 respirations per minute (RPM). In some examples, the lowest target respiration rate may be in a range of 5.5-6.5 RPM. In certain examples, a respiration rate of about 6 RPM may be advantageous for reaching a first sleep state, or drowsiness, and certain examples may provide entrainment sounds having rhythmic components associated with the respiration rate of substantially 6 RPM, e.g., cyclic rhythmic components that repeat at a rate of approximately once every 10 seconds. In some examples, the system 100 may allow the user to configure a lowest target respiration rate, or a lowest target respiration rate may be based upon a sleep history, e.g., maintained by the system 100, such as a historical average of respiration rates at the time of sleep onset, for the user, in prior sleep sessions. In some examples, a lowest target respiration rate may be even lower than those described above.

In some examples, the system 100 produces entrainment sounds including a rhythmic component associated with a target breath architecture. The target breath architecture may be a fixed breath architecture, or may be variable and may be based upon any combination of a baseline and/or historical average breath architecture (e.g., of the user), a current target respiration rate, a stage of the current sleep session (e.g., how far into the sleep session, expected sleep onset, etc.), norms for the user's physiological characteristics (e.g., height, weight, age, gender, etc.), or other factors.

In various examples, the system 100 produces entrainment sounds for a fixed amount of time, which may be based upon a configuration, which may be user selectable, and/or a historical sleep record for the user. In certain examples, the system 100 may produce entrainment sounds for a fixed amount of time of substantially 20 minutes, or in a range of 15-25 minutes, or a range of 18-22 minutes. In various examples, the system 100 may produce entrainment sounds for a fixed amount of time anywhere in a range of 10-30 minutes, and the fixed amount of time may be user configurable. In certain examples, the system 100 may produce entrainment sounds for a fixed amount of time of substantially 15 minutes, or in a range of 12-18 minutes. In various examples, the system 100 may produce entrainment sounds for a variable amount of time, such as may be based upon feedback regarding the user's active respiration character and/or sleep state, as described in greater detail below.

In various examples, the system 100 may produce other sounds intended to enhance or maintain a sleep state after the expiration of a period of entrainment sounds, whether a fixed or variable period of entrainment sounds. Such other sounds may include soothing sounds, e.g., such as sounds expected to promote relaxation. Such other sounds may additionally or alternatively include masking sounds, such as sounds expected to conceal, cover-up, or mask undesirable sounds in the environment. For example, air conditioners, fans, refrigerators, outside noise, street noise, wind, or another user's snoring, and others, that could disturb a user's sleep state. Masking sounds may reduce the likelihood that such undesired sounds will disturb the user's sleep state. Masking sounds may be selected or produced by the system 100 based upon an analysis of ambient sounds, and by selecting, arranging, or mixing complementary sounds.

In various examples, the system 100 may produce other sounds along with entrainment cues, such as soothing or other underlying sounds and/or masking sounds. For example, soothing sounds may be produced as an underlying sound to an entrainment sound (e.g., at lesser volume), or the soothing sounds may be superior (e.g., at higher volume) to the entrainment sound. The system 100 may accommodate user configuration of soothing sounds, including selection of types of soothing sounds and/or audio files, and relative volume between soothing sounds and entrainment sounds.

Entrainment cues include a rhythmic component to which a user is intended to match his/her respiration rate. In various examples, the rhythmic component of an audible cue may be related to a tempo of an audio composition or may be a prominent sound element within a soundscape (e.g., such as a frog in a forest scene, a wave in a beach scene, etc.), may be a component incorporated into a soothing sound, or may be an independent sound or have other character. The entrainment sound, or the rhythmic component thereof, for example, may be the sound of a person breathing, or may be an audible instruction to "breathe in, breathe out," or may be any of numerous other options. In various examples, any rhythmic component with a repetitive cycle on the order of human respiration rate may serve as the active component of an entrainment cue or sound. Further, in various examples, the rhythmic component may include sub-components of the repetitive cycle to indicate portions of a breath architecture (inhale, exhale, and optional holding periods). Accordingly, a rhythmic component, which may be audible, visible, or tactile, may provide cues for both respiration rate and breath architecture.

The system 100 may allow user selection of various options for entrainment sound, such as sound type, audio file, register, tone, volume, etc. Additional options for entrainment sounds may be configurable, loadable, downloadable, upgradeable, purchasable, etc., and may be provided by a remote server or via a remote or local storage capability. In some examples, the system 100 may be configured with a routine to play differing entrainment sounds over a number of sleep sessions, and to monitor the user's performance, such as how quickly he/she falls asleep, to determine one or more entrainment sounds that work well for the user.

In various examples, the system 100 includes a biometric sensor 130 or includes an interface to which such a biometric sensor 130 may be coupled. The biometric sensor 130 provides information regarding a user. For example, a biometric sensor 130 may provide information about respiration rate, heart rate, heart rate variability, blood pressure, blood oxygen levels, etc., and such information may be based upon, or derived from, various physical sensors that may involve any of numerous technologies including accelerometry, reflectometry and/or backscatter of various signals (e.g., laser, radio frequency, millimeter wave, etc.), such as off the user's body or skin to detect motion, acoustics (e.g., microphones to detect breathing, snoring, heartbeat, etc.), EEG, EKG, ECG, or others. When a biometric sensor 130 is included, various examples of the system 100 may adjust entrainment cues based upon feedback provided by, or derived from, the biometric sensor 130 (e.g., closed loop).

Accordingly, in various examples, the system 100 may have or receive information regarding the user's respiration. The system 100 may adjust the entrainment cues to a target respiration character, such as to a target respiration rate that is lower than the user's current respiration rate, or to a target breath architecture that may be expected to enhance onset of a desired result (e.g., sleep, relaxation, meditation, etc.). If the user achieves the target respiration character, or within some threshold of the target respiration character, for some time threshold, the system 100 may adjust the entrainment cues for a new target respiration character. In some examples, a target respiration rate is lowered, and the target respiration rate may be limited to a lowest target respiration rate, e.g., in accord with those described above, and not adjust the entrainment cues for lower target respiration rates once the user has achieved the lowest target respiration rate.

In some examples, the system 100 may produce entrainment cues without information about the user's respiration rate (e.g., open loop), such as for a fixed or pre-configured amount of time.

In various examples, upon detecting that a user has fallen asleep, or has achieved a certain level of drowsiness, the system 100 may transition to a mode in which the system 100 produces reduced entrainment cues (such as lower volume sounds, dimmer lights, reduced haptic intensity, etc.) or ceases producing entrainment cues. In various examples, system 100 may transition to masking sounds, may continue or transition to soothing sounds, or may cease producing sounds, any of which may be configurable by the user and/or may be determined on the basis of the user's current respiration or sleep performance, historical sleep performance (e.g., a sleep log as discussed in more detail below) and/or may be based on other acoustic sounds, such as undesired noise, snoring, etc. Such transitions may be gradually implemented, such as by fading out audio that will no longer be produced and/or fading in new audio that will be produced and/or crossfading between selected audio content.

In various examples, the system 100 may record a sleep log, e.g., in the memory 114, which may include historical data regarding a user's respiration rate and/or breath architecture relative to absolute time, time relative to a start of entrainment, time since a previous adjustment of a target respiration character, time interval maintained at a certain respiration character, and so on. In some examples, the system 100 may establish a lowest target respiration rate based upon the user's lowest historical respiration rate (e.g., from the sleep log) or various average(s) of the user's lowest historical respiration rates. Accordingly, a lowest target respiration rate may be custom to the user and may be higher or lower than the lowest target respiration rates previously described. In various examples, the system 100 may begin entrainment at a pre-configured default initial respiration rate and may include a pre-configured default lowest target respiration rate, and may transition through various intermediate target respiration rates, e.g., as the user progresses to and matches each target respiration rate, until the user falls asleep.

The system 100 may further adjust the initial target respiration rate and/or the lowest target respiration rate according to stored data maintained in the sleep log, e.g., regarding prior sleep sessions for the user. For example, if the user's respiration rate quickly matches or goes lower than the initial target respiration rate, the system 100 may establish a new value as the initial target respiration rate for the user. If the user often falls asleep well before the system 100 has reached the lowest target respiration rate, or if a particular target respiration rate tends to successfully cause the user to fall asleep, the system 100 may establish a new value as the lowest target respiration rate for the user. In various examples, default values of any target respiration rate may be based upon user physiology information such as gender, height, weight, age, etc., which may be gathered by user interaction with the system 100 or by interaction or integration with a third-party application and/or device, e.g., a smart scale, a fitness tracker, etc.

In various examples, the system 100 may include one or more microphone(s) 160. The microphone(s) 160 may be a component of the biometric sensor 130, or may contribute to biometric information from such a biometric sensor 130, e.g., to detect breathing, snoring, etc. The microphone(s) 160 may be a component that enables, at least in part, a voice control feature of the user interface 140. The microphone(s) 160 may be a sensor to detect or determine various acoustic sounds in the environment, which may include breathing, snoring, undesired sounds such as mechanical noise, conversations, etc. The system 100 may include one or more other sensor(s) 170, such as to detect various environmental parameters. For example, the sensor(s) 170 may provide information about temperature, ambient light, air quality, humidity, etc. In various examples, the system 100 may include various interfaces to which a microphone 160, a sensor 170, or any number of these may be coupled.

Various examples may include a network interface 180. The network interface 180 may be any of various interfaces for network communication, and may be wired (e.g., ethernet, IEEE 802.3) or may be wireless (e.g., Bluetooth®, wi-fi, any of IEEE 802.11). Certain examples of the system 100 may include numerous network interfaces. For example, a system 100 may have a wired or wireless interface for coupling to a local area network and may also have a Bluetooth® interface for pairing to local wireless devices. A network interface 180 may be a communications interface of any of numerous types as are known in the art. Accordingly, the network interface 180 may enable, at least in part, a smartphone 142 to provide some or all of the user interface 140 and/or the display 150 functionality. The network interface 180 may also provide communication capability to various network or cloud components, such as connected or smart home components (e.g., thermostat, lights, remote speakers, etc.) or remote data processing and/or storage (e.g., via the internet).

Various examples may include an audio source 190 or an audio input 192, from which various audio signals may be received for playback. Such audio signals may include entrainment sounds, soothing sounds, masking sounds, or general audio content (e.g., music, news, commentary, sports, etc.). For example, the audio source 190 may be a disc player, a radio tuner, a memory card, or any of various memory systems and/or readers capable of storing and/or retrieving audio signals from media, or other audio sources. In various examples, the system 100 may include one or more such audio sources 190 and/or audio interfaces 192 to which an audio source 190 may be coupled.

Various examples are directed to systems and methods that use audio having a rhythmic component to which a user is intended to entrain, or match with, the user's respiration. In some examples, a visual indicator (e.g., lights, optics) or display may be used to provide a rhythmic or repetitive component to which the user is intended to entrain, with or without an audible component, and in some examples a haptic, vibratory, or other tactile indicator may be used to provide a rhythmic or repetitive component to which the user is intended to entrain. Various examples may use one or more of such sensory modes as an indicator to provide an entrainment cue. While various systems and methods described herein are described with respect to an entrainment sound, such other sensory modalities and forms of user-discernible indicators are equally intended to be contemplated by the examples described. Accordingly, the term "entrainment sound" as used herein (above and below) includes other forms of "entrainment cue" unless the context clearly indicates otherwise. Accordingly, examples of the system 100 may not include a speaker 120 and/or may include components capable of providing other forms of entrainment cues, such as lights, displays, and haptic elements, among others.

In various examples, a system or method may include various modality combinations of providing entrainment cues. For example, an audible and visible cue may be provided during a sleep session, but as the user's respiration matches various target respiration characteristics, either of the visible or the audible component of the entrainment cues may be phased out, leaving only the other. Various examples may incorporate the same for any combination of the various modalities described. Additionally, various modalities may be added and/or removed, faded in or out, to accommodate user options, configuration, historical performance, or learned information from various studies or research (of the user or the general population) regarding what modalities may optimally enhance a desired end state (e.g., sleep, relaxation, meditation, etc.).

When a user matches his/her respiration to a rhythmic or repetitive component, e.g., entrainment cues, such may be beneficial to reducing an amount of time it takes for the user to fall asleep. For many individuals, there may be a significant amount of time from when the user begins to attempt going to sleep until the user actually falls asleep. When the user actually falls asleep may be termed "sleep onset," and an amount of time it takes the user to reach sleep onset (e.g., how long it takes to fall asleep) may be termed "sleep latency."

A precise definition of sleep onset is not available, at least in part because falling asleep is a process, but most individuals first enter a shallowest stage of NREM (Non Rapid Eye Movement) sleep, referred to herein as stage N1. In such shallowest stage of NREM sleep, it may be very easy to wake an individual, and the individual may even feel that he or she was not sleeping. Because the shallowest (N1) stage of sleep may be marked by significantly decreased attentiveness, yet is a stage from which an individual may be easily awoken, the term "drowsiness" may be used herein as an equivalent descriptor of N1 stage sleep, or to refer to the moment of entering N1 stage sleep and/or a brief period of time just prior to or after entering N1 stage sleep.

Various stages of NREM sleep may be defined by various levels of brain activity, heart rate, heart rate variability, respiration rate, and other biological metrics. N1 stage sleep is considered the shallowest NREM stage of sleep. The next deeper stage of NREM sleep is referred to herein as stage N2. The term "falling asleep" may be associated with entering into N1 stage of sleep, while "being asleep" may be associated with sustained N1 and all other stages of sleep. As above, "drowsiness" may be used herein as substantially synonymous with "falling asleep" or entering N1 stage of sleep. Having fallen asleep, and passed through an N1 stage of sleep, many individuals may transition between various stages of NREM and REM sleep without returning to N1 stage of sleep, and returning to N1 stage sleep may be less likely the longer the individual has been asleep.

In various examples, a system 100 may detect a user's entry into N1 sleep by various means. In certain examples the system 100 may monitor a user's respiration rate for a change, such as a sudden or a significant change, or departure from the entrainment rate (e.g., a target respiration rate). For example, the onset of sleep may cause the user to lose focus on his/her active entrainment, and his/her respiration rate may change. In certain examples, a target respiration rate associated with an entrainment sound may be a relatively low respiration rate, and a user's sleep onset may cause him/her to no longer match the entrainment sound, e.g., to no longer maintain the relatively low respiration rate, possibly due to loss of concentration, and may transition to a higher respiration rate associated with the user's N1 stage of sleep.

Accordingly, various examples in accord with those described herein may detect a variance in respiration rate, e.g., away from the target respiration rate associated with an entrainment cue, as an indication that a user has fallen asleep or is falling asleep. In some examples, a threshold variance may be applied. In some examples, an amount of change in respiration rate may be compared to a threshold. In some examples, an amount of change in respiration rate within a threshold amount of time may be taken as a criterion that the user has fallen asleep. In some examples, an amount of time over which the user's respiration rate substantially does not move toward a target respiration rate, e.g., the user is no longer trying to entrain, may be taken as an indicator that the user has fallen asleep. Transition of the user's respiration rate, away from a target respiration rate, may be abrupt in some examples. Accordingly, a threshold respiration rate variance, optionally within a threshold amount of time, may be interpreted by the system 100 as an indication that the user has fallen asleep, in various examples.

Accordingly, during a period that the system 100 produces entrainment cues, and the user is still awake, a detected respiration rate (e.g., via the biometric sensor 130) may generally move toward or match a target respiration rate associated with the entrainment cues. The system 100 may then interpret a shift in the user's respiration rate as an indication of sleep onset. In various examples, the system 100 may determine or detect onset of drowsiness as a user's respiration rate drifts up after a period of entrainment during which the user's respiration rate moved toward matching the entrainment cues. More generally, drift of a user's respiration rate from that of entrainment matching, especially after a period of successful or observed entrainment matching, may be interpreted by the system 100 as the user having fallen asleep. The biometric sensor 130 may provide (directly, or by further processing) real-time or near-real-time information on the user's respiration, which may provide benefits of a closed loop entrainment system, as in various examples of the system 100.

Improvement in sleep over a number of sleep sessions is a desired goal in some instances. Various metrics may be used to determine an improvement in sleep. Entrainment may be associated with getting to sleep, and improvement in sleep due to entrainment may be measured in various examples by latency metrics, e.g., the time taken to achieve falling asleep. Four non-limiting examples of such metrics are presented in Table 1.

TABLE 1

| Metric 1 | Drowsiness Latency | Time until user enters N1 stage |
| Metric 2 | Stable Drowsiness Latency | Time until user enters a sustained N1 stage |
| Metric 3 | Sleep Latency | Time until user enters N2 stage |
| Metric 4 | Stable Sleep Latency | Time until user enters a sustained N2 stage |

In various individuals, using entrainment features may achieve a 30% or greater improvement in each of the above metrics. Further, such an entrainment feature is more effective at reducing time to reliably fall asleep than is listening to soothing sounds alone. Generally, these statements are effective regardless of a user's severity of sleep issues, e.g., whether an individual has an objective sleep problem (e.g., mean sleep latency of greater than 20 minutes) or merely self-reports as having difficulty falling asleep, due to anxiety, racing thoughts, etc.

Figure 2:
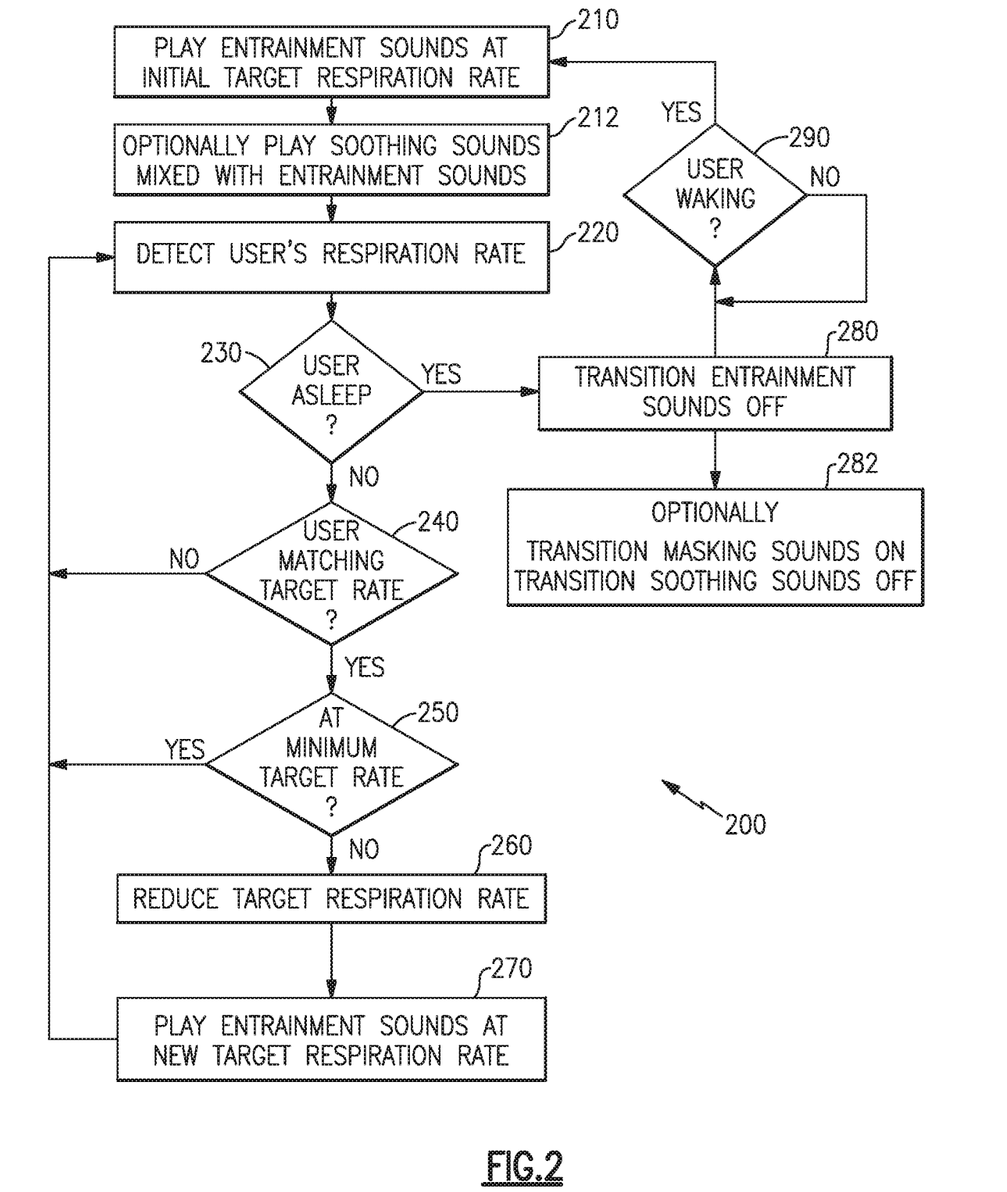
FIG. 2 is a flow diagram of an example method performed by the system of FIG. 1.

FIG. 2 illustrates a flow diagram of an example method 200 of providing entrainment that may be performed by the system 100. The system 100 may play entrainment sounds (block 210) at an initial target respiration character, which may be a respiration rate and/or breath architecture. The system 100 may also play soothing sounds (block 212) along with the entrainment sounds, e.g., based upon user configuration, selection, etc. In some examples, entrainment sounds may be adjusted in volume, e.g., relative to the soothing sounds, to maintain effectiveness. In certain examples, the entrainment sounds may be adjusted in volume within particular frequency bins affected by the soothing sounds, e.g., equalization of either of the entrainment sounds or the soothing sounds may be adjusted to enhance the effectiveness of either in the presence of the other. The system 100 detects the user's respiration (block 220), e.g., based upon input from the biometric sensor 130, and uses biometric information to determine whether the user's respiration has matched the target respiration rate and/or breath architecture, or whether the user has fallen asleep.

Various examples may include logging respiration data over time to provide a sleep record from which sleep reports may be generated and/or from which future sleep sessions may be optimized. For example, during one sleep session, the system 100 may determine that the user quickly matches the initial target respiration character, or a lower respiration rate, or that the user takes a long time to match the initial target respiration character, and in response the system 100 may modify the initial target respiration character for future sleep sessions, e.g., based upon analysis of the sleep record. Similarly, in some examples, the system 100 may determine that the user often falls asleep during playback at a particular target respiration rate or breath architecture and in response the system 100 may establish such as the lowest target respiration rate or final target breath architecture for future sleep sessions, or may establish the lowest target respiration rate as an amount, e.g., one step, lower than that at which the user most often falls asleep, or may prompt the user whether to establish one of these as the lowest or final target respiration character, etc. In various examples, the system 100 may analyze a sleep record from a previous night, or across a range of previous nights, and may establish various parameters, e.g., initial and lowest target respiration rates and/or initial and final breath architecture, as well as other parameters, based upon the previous night(s), e.g., sleep session(s). Accordingly, the system 100 may anticipate that a sleep session by a particular user may have similar characteristics to the user's prior sleep sessions. Further, the system 100 may modify various parameters to attempt mild improvement to the user's sleep sessions, or sleep quality, over a number of sleep sessions. In some examples, the system 100 may maintain a record of differing types of sessions for a particular user, such as daytime nap sessions and/or meditation or relaxation sessions versus overnight sleep sessions.

As described above, the system 100 detects the user's respiration (block 220), and may use other biometric information, to determine whether the user's respiration has matched the target respiration character or whether the user has fallen asleep. Accordingly, the method 200 may determine whether the user has fallen asleep (block 230) and/or whether the user has matched the target respiration rate (block 240). If the user has not yet matched the target respiration rate, the method 200 may continue detecting the user's respiration (block 220) while continuing to play the entrainment sounds. If the user has matched the target respiration rate, the method 200 may proceed to lower the target respiration rate, if appropriate. For example, if the target respiration rate is already at the lowest (minimum) (block 250) target respiration rate (as described in more detail above) the method 200 may continue detecting the user's respiration rate (block 220) while continuing to play the entrainment sounds at the current target respiration rate, e.g., without lowering the target respiration rate. If the current target respiration rate is not at the lowest target respiration rate (block 250), the method 200 may reduce the target respiration rate (block 260) and transition to playing the entrainment sounds at the new (lower) target respiration rate (block 270).

In some examples, the method 200 may wait an amount of time before transitioning to the new (lower) target respiration rate. The amount of time may be configurable, and may be variable, and may be based upon how quickly the user matched the current target respiration rate. A transition to the new (lower) target respiration rate may be gradual, such as by gradually slowing the rhythmic component, for example. In some examples, the system 100 may maintain a timer of how long a particular target respiration rate has been in effect and may reduce the target respiration rate based upon reaching a maximum amount of time, rather than or in addition to the user having matched the target respiration rate. In some examples, the system 100 may be configured (or may be a user selectable option) to reduce the target respiration rate below the lowest target respiration rate, such as when the user has been matching the lowest target respiration rate for some time yet has not fallen asleep. In some examples, the system 100 may be configured (or may be a user selectable option) to increase the target respiration rate when the user has been matching the lowest target respiration rate for some time yet has not fallen asleep, as such may re-engage the user to concentrate on entrainment.

If at any time it is detected that the user has fallen asleep (block 230), the method 200 may turn off or cease producing/playing the entrainment sounds (block 280), optionally with a gradual transition, such as slowly reducing the volume of the entrainment sounds, e.g., fading out. The method 200 may also stop playing soothing sounds, or may start playing soothing sounds, and/or may start playing masking sounds (block 282), based upon various criteria such as user configuration and/or acoustic or other environmental conditions in the sleeping environment, and such transitions may also be gradual, e.g., fade-in, fade-out, cross-fade.

In some instances, a user may begin to re-awaken after having fallen asleep. In some examples, the method 200 may monitor for the user waking (block 290) and may be configured to return to a mode of providing entrainment sounds (e.g., block 210) to encourage the user to get back to sleep. Entering the mode of playing entrainment sounds after detecting that a user is waking up may include playing the entrainment sounds with a "new" initial target respiration character (e.g., rate and breath architecture). For example, the initial target respiration rate when re-starting an entrainment mode after detecting the user waking up may be the same initial target respiration rate as used when a user first lays down to sleep, or may be the last target respiration rate in operation before the user fell asleep, or may be based upon the user's respiration rate when it is detected that the user is waking up, or may be any combination of these or other bases for establishing a "new" initial target respiration rate. A "new" initial breath architecture may be selected or established in like fashion. In various examples, the method 200 may return to a mode of providing entrainment sounds, after having detected the user waking up, based upon additional criteria, which may include user configuration, time of day (e.g., whether it is approaching time to wake up anyway), length of the sleep session thus far, and/or other criteria. In various examples, the system 100 may detect the user waking by interpretation of biometric sensor data and/or by the user taking a certain action, such as pressing a button, speaking a command, or selecting an option associated with the user interface 140.

The method 200 is one example of a method that may be implemented by a system in accord with aspects and examples herein. Numerous variations of components and order of operations of the method 200, and of details of implementing each, will be apparent to those of skill in the art with the benefit of this disclosure. Further details of at least one example of operation of a system, such as various examples of the system 100, are described in more detail below.

As described herein, in various examples, the system 100 may produce entrainment cues having a rhythmic component matching a target respiration rate and/or breath architecture. The target respiration rate at any given time may be based on the user's actual respiration rate (e.g., in RPM's), e.g., as indicated by the biometric sensor 130. For example, the target respiration rate may be based upon the user's respiration rate averaged over a trailing period of time, in some examples. Further, the target respiration rate may be a value somewhat lower than the user's respiration rate, to encourage the user to further reduce his or her respiration rate. In some examples, the system 100 may provide an indicator, such as an audible or visible indicator, when the user is determined to have matched the target respiration rate (e.g., within some threshold criterion). Accordingly, an indicator such as an audible "ding" or chime may act as a reward or signal to the user that he/she has successfully matched the target respiration rate.

In various examples, the system 100 or the method 200 may include detection of the user getting ready for bed. For example, a sensor may detect the presence of the user in bed.

Further, the user's presence may be detected or confirmed by breathing, e.g., the system 100 or the method 200 may monitor a microphone signal to detect or confirm the presence of the user. For example, a user getting into bed may be detected by either or both of a presence sensor and a microphone sensor. Accordingly, the system 100 or the method 200 may exclude false triggers, such as a pet jumping on the bed. In various examples, the system 100 or the method 200 may detect when to begin producing entrainment cues (e.g., at the initial target respiration rate) based upon input from the user, such as voice command, button press, etc.

Further, the system 100 or the method 200 may detect if the user leaves the bed, such as to use a restroom or get a glass of water. In various examples, the system 100 or the method 200 may re-start to play entrainment sounds at the initial target respiration character (e.g., block 210) upon detecting the user's return, or may continue with entrainment sounds at the previous target respiration character, or may establish a new target respiration character between the initial and the previous rates and/or breath architectures, or may be configurable by the user and/or informed by analysis of prior sleep sessions, or any combination of these or other conduct. For example, a target respiration character upon a user's return to bed may be based upon a historical respiration character from previous sleep sessions, e.g., the user's typical respiration rate and/or breath architecture after returning to bed, which may depend upon prior conditions of the system 100 or the method 200, which may include time of day information, when the user got up.

In various examples, an initial target respiration rate may be a fixed initial rate, a user-configurable initial rate, or may be based upon the user's trailing average respiration rate during a startup period, or determined over a number of prior periods (e.g., average of previous evenings), or based upon a baseline period or session, or any combination of these or other bases. In some examples, the initial target respiration rate may be somewhat lower than any of these examples, such as a number of RPM less or a percentage less. Generally, the user may be expected to entrain his or her respiration rate to the target respiration rate, which may be further lowered in response to the user achieving the target respiration rate. Accordingly, an initial target respiration rate may be considered a maximum target respiration rate. In various examples, however, the system 100 may at times increase the target respiration rate, e.g., in response to the user being unable to match the target respiration rate within a certain threshold or within a certain period of time. In some examples, the user interface 140 may accommodate input from the user indicating that the system 100 should increase or decrease the target respiration rate.

In various examples, entrainment sounds produced by the system 100 may have a higher initial volume, and the system 100 may decrease the volume of the entrainment sounds as time goes by. For example, as the user's respiration rate and/or breath architecture begins to match the target respiration rate and/or breath architecture (associated with the rhythmic component of the entrainment sounds), such may indicate increased relaxation as the user moves toward falling asleep. Accordingly, the system 100 may decrease the volume of the entrainment sounds in response thereto. In some examples, the system 100 may additionally or alternatively base volume on other indicators of the user's biometric condition(s) and/or on detected environmental conditions, e.g., noises, light, temperature, etc.

In various examples, the system 100 may control the closed loop entrainment experience with a goal to reduce the breathing rate of the user to a low-end respiration rate of Y RPM, such as may be the lowest target respiration rate described above, to aid the sleep onset process. In various examples, the system 100 may iteratively lower the target respiration rate, by reducing or slowing down the rhythmic component of the entrainment cues. Accordingly, the system 100 may alter the target respiration rate to change from a respiration rate of N to N-X, where X is an increment value. In some examples, the incremental value X may be a fixed number, and in certain examples may be a fixed number in the range of 0.5 to 1.5 RPM, or in the narrower range of 0.8 to 1.2 RPM, or may be approximately 1.0 RPM. Other examples may include differing values of X, and the incremental value X may be configurable. Further examples may include non-fixed values of X. For example, the incremental value X may be a percentage of the current target respiration rate, e.g., some fraction or multiplier of N.

In various examples, the system 100 may change the target respiration rate from N to N-X once the user has matched the current target respiration rate. In various examples, the user may be deemed to have matched the target respiration rate when the user's respiration rate, optionally averaged over a trailing period of time, is within a certain threshold of the target respiration rate. In some examples, the user's respiration rate (or average thereof) may be required (by the system 100) to be within a certain threshold of the target respiration rate for a certain period of time. In various examples, the user's respiration rate variance may be required (by the system 100) to be within some variance criterion when compared with the target respiration rate.

In some examples, a variance criterion may be dynamic. In some examples, the initial criterion is a set value, but the value may be changed based on the user's ability to meet the criterion. User efforts to lower their respiration rate may provide relaxation benefits regardless of their ability to match the entrainment rate, as trying to match the entrainment rate may reduce respiration rate even when the user is not successful at matching the entrainment rate. Accordingly, the system 100 may relax a variance criterion, causing the system 100 to move on to a lower target respiration rate even if the user is not closely matching the current target respiration rate.

In some examples, a maximum time period may be imposed by the system 100 on a particular target respiration rate. Accordingly, the system 100 may reduce the target respiration rate (e.g., block 260), e.g. reducing the target respiration rate from N to N-X, after a certain amount of time has passed, regardless of whether the user has matched their respiration to the current target respiration rate, N.

In various examples, a transition to a lower target respiration rate (e.g., block 270) may include a gradual transition. The rhythmic component of the entrainment cues may be gradually reduced in time to a slower, longer period of each repetitive cycle, and the change may be implemented over numerous cycles of the repetitive content, by various examples of the system 100.

Various examples may use various methods of establishing a value for the initial target respiration rate. In some examples, the initial target respiration rate may be fixed, such as substantially about 15 RPM, or may be in a range of about 12 to 18 RPM. In some examples, the initial target respiration rate may be variable or dynamic. For example, different users may find different values most suitable, and there may be variation between values that work best for users of differing weight, gender, age, etc. Accordingly, some examples may establish a default value for the initial target respiration rate based upon any of a fixed value, a baseline respiration rate determined from a training or initial configuration routine, user physiology information (such as gender, height, weight, age, etc., which may be gathered by user interaction with an app, or integration with a third-party application, e.g., a smart scale, a fitness tracker, etc.), and/or the user's past entrainment performance.

In various examples, once the lowest target respiration rate is reached, e.g., the system 100 is producing entrainment cues at the lowest target respiration rate (e.g., "yes" at block 250), the system 100 may continue to produce the entrainment cues at the lowest target respiration rate until the user experiences sleep onset. In other examples, the system 100 may produce the entrainment cues at the lowest target respiration rate for a fixed amount of time, after which an optional transition to masking sounds or soothing sounds may be made. In various examples, the system 100 may be configured to allow user configurable options as to the lowest target respiration rate, how long to produce entrainment cues at the lowest target respiration rate (e.g., fixed time, how much time, or until sleep), and what functions to perform afterward (e.g., soothing or masking sounds, environmental adjustments, etc.).

Various examples may use various methods of establishing a value for the lowest target respiration rate. In some examples, the lowest target respiration rate may be fixed, such as substantially about 6 RPM (e.g., a ten second breathing cycle). In some examples, the lowest target respiration rate may be variable or dynamic. For example, different users may find different values most suitable, and there may be variation between values that work best for users of differing weight, gender, age, etc. Accordingly, some examples may establish a default value for the lowest target respiration rate based upon any of a fixed value, a baseline respiration rate determined from a training or initial configuration routine, user physiology information (such as gender, height, weight, age, etc., which may be gathered by user interaction with an app, or integration with a third-party application, e.g., a smart scale, a fitness tracker, etc.), and/or the user's past entrainment performance (e.g., the user's respiration variance with respect to the target respiration rate during prior sleep sessions, or at each interval of prior target respiration rates during the current sleep session, for example).

In some examples, the system 100 may be configured to detect a large increase in respiration rate variance, e.g., relative to a target respiration rate, which may indicate that the user is experiencing sleep onset. In such conditions, the system 100 may be configured to maintain the current target respiration rate as the lowest target respiration rate, e.g., until the user falls asleep.

In various examples, other biometric information may be used by the system 100 to determine an optimal target respiration rate, and the system 100 may establish such rate as the lowest target respiration rate. For example, a boost in heart rate variability (HRV) may be sensed (e.g., by the biometric sensor 130 or other sensor) and may serve as an indicator that a user is at an optimal respiration rate for sleep. Accordingly, the system 100 may produce entrainment cues to maintain the user's respiration rate, e.g., set it to be the lowest target respiration rate.

In various examples, respiration and other biometric information may be used by the system 100 to detect the occurrence of sleep onset. Such information may also be used to provide improved sleep staging, that is, transitions between entrainment, masking or other activity at varying user sleep stages, and wake-up, that may thereby be more accurately matched to the user's true sleep state. Accordingly, some examples may determine or select audio to be played based upon a current sleep stage and/or a detected or anticipated transition in sleep stage and/or a detected or intended waking.

Sleep onset is the first sleep stage experienced after a stage of wakefulness (stage W). Most often the first sleep stage is either N1 or N2. Sleep stage N1 is often described as being characterized by slow eye movement (SEM), low amplitude mixed frequency activity, vertex sharp waves (V waves) cortical arousals, and micro-arousals. Sleep stage N2 is often described as being characterized by high sigma and alpha activity, K complex, and sleep spindle. Various of these characteristics may be detected with various biometric sensors, such as EEG or the like, and various examples of a system 100 may include such sensors, or be configured to receive such information, and to use the biometric information to detect or determine various sleep stages.

Various examples of the system 100 may not have access to the biometric information described above. Various examples may detect or receive information about a user's respiration, however, as described above. Accordingly, various examples may detect drowsiness and/or sleep onset based upon user respiration information. For example, a user's ability to match to the entrainment cues may decline as the person becomes drowsy and stops paying attention or drifts off. A user may undergo a rapid increase in respiration rate during sleep onset, or once he/she is asleep, following a period of entrainment. These behaviors can be used to determine sleep onset when the user is using the entrainment process and the biometric sensor provides respiration information.

In various examples, the system 100 may analyze variance in the user's respiration rate for various purposes. For example, the system 100 may evaluate the user's respiration rate variance relative to the current target respiration rate, using a variance criterion. The system 100 may evaluate the user's prior respiration rate variances at prior target respiration rate values (i.e. N+1, N+2, etc.), against a variance criterion and with respect to the current target respiration rate. For example, such analysis of respiration rate variance may indicate how closely the user was able to match prior target respiration rates. Comparison may also be made with prior sleep sessions, e.g., how closely did the user match target respiration rates during prior sessions of falling asleep. Accordingly, certain examples of the system 100 may be configured to use historical information to establish a criterion, e.g., a variance criterion, for determining whether a user has matched a target respiration rate or has fallen asleep.

Accordingly, such information and values may be used as additional inputs to determine whether the user is experiencing drowsiness or has entered sleep onset. For example, a sudden increase in respiration rate variance relative to the variance at previous target respiration rate values, or relative to the variance during previous sleep sessions, may indicate sleep onset, or a respiration rate variance above a specific threshold may indicate sleep onset as soon as it is observed.

Various examples of a system 100 may detect a shift in mean respiration rate. In addition to or instead of analyzing variance against a target respiration rate, sleep onset may be indicated by a rapid shift in the user's mean respiration rate. For example, a user's respiration rate being X RPM during minutes 1-5 of the entrainment process, then shifting to a significantly greater rate Y RPM during minutes 6-10. The large increase in rate may indicate sleep onset.

Where thresholds are used, either in absolute variance or in mean RPM, the value may be predetermined, or may be adjusted based on inputs provided by the user, which may include physiological information such as height, weight, age, or gender, or may be adjusted based on historical data gathered by the system, or any combination of these, in various examples. When users entrain their breathing to a reference (e.g., sounds, lights), a good predictor of drowsiness and entering a sleep state may be that their ability to match their breathing to the reference "drifts" (e.g., their ability becomes worse), e.g., compared to prior time periods. This phenomenon may be used, during paced breathing or entrainment, as part of a detection of drowsiness and sleep onset, as well as to improve the sleep experience itself by using this information to modify the reference (e.g., adjust the target respiration rate of the entrainment sounds) or by controlling connected consumer devices that may be tied to sleep behaviors.

For example, one or more sensors may measure a person's breath rate as they attempt to match an entrainment reference. This reference may be displayed in different ways, such as via sounds or lights, including the entrainment sound mentioned above. The user's ability to match their breath rate to the entrainment reference is measured over time, as well as how this ability changes across intervals throughout a time period or sleep session. When the user's matching ability declines by a certain level, such may signal that the user has become drowsy or become inattentive while falling asleep. Various measurements of declined ability that may identify drowsiness or sleep onset may be calculated in different ways, such as via a prescribed value, via historical data collected from the individual, or via norms for the group in which the person belongs or a general population norm.

In various examples, the system 100 may take any of various actions upon identifying drowsiness or sleep onset. The system 100 may create a marking of drowsiness or a sleep state in a sleep report, by itself or when used in conjunction with other physiological data.

In response to identifying drowsiness or sleep onset, the system 100 may modify the entrainment reference. For example, some systems in accord with those herein may use lights to indicate a desired user breathing profile, including a target respiration rate, and may modify the lights by, e.g., reduction in brightness, size, or change in hue, or implementing transition to no lights, etc. Some systems use entrainment sounds (as described in greater detail above) and may modify the entrainment sounds by, e.g., reduction in volume (or relative volume to background sounds); implementing transition to silence; or implementing transition to other kinds of sounds (e.g., masking sounds).

In response to identifying drowsiness or sleep onset, the system 100 may enact control of connected consumer electronics tied to sleep behavior or otherwise located nearby, such as by dimming screens, adjusting curtains or shades, changing a thermostat, reducing undesired sounds, etc. In some examples, the system 100 may control other audio systems, e.g., to generate soothing sounds and/or masking sounds.

In some instances, the user's ability to match an entrainment reference may improve by a certain level (using detection methods similar to those described above), which may indicate that the person has become more attentive. An increase in ability may be quantified in numerous ways, and as above a determination and/or threshold value may be based upon historical data from an individual, by group data, or by a prescribed value.

In various examples, the system 100 may take any of various actions upon identifying increased attentiveness or wakefulness. The system 100 may create a marking of wakefulness, based upon respiration rate changes alone or in conjunction with other physiological data.

In response to identifying increased attentiveness or wakefulness, the system 100 may modify the entrainment reference. For example, some systems in accord with those herein that use lights to indicate a desired user breathing profile, including a target respiration rate, may modify the lights by, e.g., increased brightness, size, or change in hue, or implementing transition from no lights, etc. Systems in accord with those herein that use entrainment sounds (as described in greater detail above) may modify the entrainment sounds by, e.g., increase in volume (or relative volume to background sounds); ceasing a prior transition to silence, or implementing transition from silence or other sounds (e.g., soothing sounds, masking sounds).

Further in response to identifying increased attentiveness or wakefulness, the system 100 may enact control of connected consumer electronics tied to sleep behavior or otherwise located nearby, such as by changing a thermostat or controlling other sounds in the environment.

Construction of entrainment cues is described in greater detail below. Beyond using a generally rhythmic sound to entrain respiration, more specific and detailed sounds or cues may be constructed dynamically, based on the user's actual respiration patterns. An optimal respiration architecture may be based on information about a person's natural inhale/exhale, and potentially hold, ratios, measured either before guided breathing or during a guided breathing session, for instance. In various examples, entrainment cues may have portions corresponding to such phases of the respiration cycle, such that the user can match not only the respiration rate per minute of the entrainment cue but can also match the breath architecture. In various examples, the system 100 may measure a user's breath architecture during operation. Accordingly, the system 100 may dynamically adjust ratios based on a user's response during the entire experience, rather than implementing a fixed breath architecture based on a priori assumptions.

In order to maximize the effectiveness of the entrainment experience, the breathing architecture of the entrainment cues produced by the system 100 may be optimized. This optimization may be accomplished by the system 100 by matching the user's natural breath architecture (e.g., based upon real-time detection, a baseline session, or user input), adjusting for the user's prior ability to match the architecture of the entrainment cues, adjusting for the user's variation in architecture at differing respiration rates (e.g., based upon performance against earlier target respiration rates within the same sleep session or prior sleep sessions), or based upon physiological norms without regard to the user's actual breath architecture, or any combination of these or other bases.

For example, the entrainment cue may include a respiration architecture that matches the user's natural architecture. The user's natural breath architecture may be measured during entrainment, e.g., via the biometric sensor 130 or other sensor, or may be measured outside of the entrainment process, such as during an initial calibration or setup process when the user is not attempting to fall asleep.

In some examples, the respiration architecture produced by the system 100 may match the user's breath architecture as informed by each of the target respiration rates experienced during the entrainment process, e.g., during the instant sleep session, or prior sleep sessions. The respiration architecture may be modified based on the user's ability to match the breath architecture of the entrainment cues, or based on an ideal breath architecture for the desired entrainment effect, which may also depend upon the various target respiration rates the system 100 progressed through in the instant session and/or prior sessions.

In some examples, the respiration architecture produced by the system 100 may be a dynamic function of the user's respiration rate, e.g., as informed by the biometric sensor 130, but may be independent of the user's respiration architecture. For example, the user's respiration rate variance from the target respiration rate of the entrainment cue may indicate a mis-match of the breath architecture. The breath architecture of the entrainment cue may change as a direct function of the current target respiration rate, that is, as the system 100 progresses through target respiration rates.

In some examples, the respiration architecture produced by the system 100 may be a function of the user's physiology (gender, height, weight, etc.) as informed by user self-entry through a user interface or third-party application integration (e.g., connected scale, etc.) and independent of the user's measured respiration architecture.

Benefits of matching the user's own breath architecture may include making the entrainment process easier or more relaxing for the user and may ultimately improve sleep latency. Changing the respiration architecture dynamically based on the current target respiration rate may also make it easier for users to follow along as the respiration rate decreases. This can be especially beneficial in examples of the system 100 that gather information through a biological sensor 130 (or other sensor) in an automated way, reducing the amount of user interaction required and thereby enhancing ease of use, e.g., a smooth experience when getting the system 100 operational and customized.

In various examples, a configuration and/or baseline training or setup routine may be provided. For example, a "first night" mode of operation may include providing detailed instructions to a user and may allow more extensive user input to establish norms and preferences for the user and/or to validate that various sensors are operational within allowed parameters. In some examples, a configuration routine may include instructing the user to lie down and breath normally, during which the system 100 may establish a baseline breath architecture (inhale-exhale-hold) for the user. In some examples, the system 100 may not produce entrainment cues during a baseline configuration routine and may instead monitor the user to establish baseline data for the user's sleep onset, resting respiration rate and/or breath architecture, sleeping respiration rate and/or breath architecture, etc. Such data may be used to establish initial and lowest target respiration rates and/or initial and final target breath architectures for subsequent sleep sessions. The system 100 may target improvement to sleep onset or other detected sleep quality parameters, as compared to the baseline data, and may provide reports of such data. In various examples, the system 100 may accommodate user input to perform a baseline or configuration setup routine at any time, e.g., to reset the system, or a modified routine to make adjustment to established baseline values.

In various examples, a user training routine may be provided. For example, a practice or training mode of operation may include providing detailed instructions to a user and may provide entrainment cues for the user to practice matching their respiration rate and/or breath architecture. Some examples may provide enhanced or additional feedback to the user to inform the user of his or her success at matching the entrainment cues, for example. Such a training routine may be made available by the system at any time, e.g., based upon user input or selection.

The various figures illustrate functional block diagrams that may be representative of functions performed by a processor, which may include various instructions stored in a memory for performing such processes. In various examples, the various processing may be performed by a single processor or controller, or various processing functions may be distributed across numerous processors or controllers. No particular division of processing functionality across hardware processing platforms is intended to be implied by the figures.

It should be understood that many of the functions, methods, and/or components of the systems disclosed herein according to various aspects and examples may be implemented or carried out in a digital signal processor and/or other circuitry, analog or digital, suitable for performing signal processing and other functions in accord with the aspects and examples disclosed herein. Additionally or alternatively, a microprocessor, a logic controller, logic circuits, field programmable gate array(s), application-specific integrated circuit(s), general computing processor(s), micro-controller(s), and the like, or any combination of these, may be suitable, and may include analog or digital circuit components and/or other components with respect to any particular implementation Functions and components disclosed herein may operate in the digital domain, the analog domain, or a combination of the two, and certain examples may include analog-to-digital converter(s) (ADC) and/or digital-to-analog converter(s) (DAC) where appropriate, despite the lack of illustration of ADC's or DAC's in the various figures. Further, functions and components disclosed herein may operate in a time domain, a frequency domain, or a combination of the two, and certain examples include various forms of Fourier or similar analysis, synthesis, and/or transforms to accommodate processing in various domains.

Any suitable hardware and/or software, including firmware and the like, may be configured to carry out or implement components of the aspects and examples disclosed herein, and various implementations of aspects and examples may include components and/or functionality in addition to those disclosed. Various implementations may include stored instructions for a digital signal processor and/or other circuitry to enable the circuitry, at least in part, to perform the functions described herein.

Examples of the systems and methods described herein comprise computer components and computer-implemented steps that will be apparent to those skilled in the art. For example, it should be understood by one of skill in the art that computer-implemented steps may be stored as computer-executable instructions on a computer-readable medium such as, for example, hard disks, optical disks, solid-state disks, flash ROMS, nonvolatile ROM, and RAM.

Furthermore, it should be understood by one of skill in the art that the computer-executable instructions may be executed on a variety of processors such as, for example, microprocessors, digital signal processors, gate arrays, etc. For ease of exposition, not every step or element of the systems and methods herein is described as part of a computer system, but those skilled in the art will recognize that each step or element may have a corresponding computer system or software component. Such computer system and/or software components are therefore enabled by describing their corresponding steps or elements (that is, their functionality), and are within the scope of the disclosure.

Having described above several aspects of at least one example, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. An apparatus comprising:
an input configured to be coupled to a biometric sensor and to receive sensor information about respiration of a user;
an output configured to be coupled to a transducer, the output configured to provide signals to control the transducer; and
a processor coupled to the input and the output and configured to:
cause the transducer to provide entrainment cues having a rhythmic component at a target respiration rate,
determine a respiration rate of the user, based at least in part upon the sensor information, and
cause the transducer to cease providing entrainment cues responsive to determining that the user's respiration rate meets a sleep criterion,
the target respiration rate being a first target respiration rate, the processor further configured to gradually adjust the rhythmic component to a second target respiration rate lower than the first target respiration rate responsive to detecting that the user's respiration rate matches the first target respiration rate and that the user's breath architecture matches a target breath architecture, the target breath architecture defining a ratio of inhalation time to exhalation time.

2. The apparatus of claim 1 wherein the processor is configured to determine that the user's respiration rate meets a sleep criterion based upon a variance of the user's respiration rate deviating from the target respiration rate by a threshold.

3. The apparatus of claim 1 wherein the processor is further configured to detect a waking criterion and to cause the transducer to provide the entrainment cues responsive to detecting the waking criterion.

4. The apparatus of claim 1 wherein the processor is further configured to limit either of the first target respiration rate or the second target respiration rate to a lowest target respiration rate, the lowest target respiration rate being a target respiration rate beyond which the processor will not adjust the rhythmic component to be lower.

5. The apparatus of claim 4 wherein the lowest target respiration rate is within a range of 5.5 respirations per minute to 6.5 respirations per minute.

6. The apparatus of claim 4 wherein the lowest target respiration rate is based on a historical average of respiration rates at the time of sleep onset of the user.

7. The apparatus of claim 1 further including a timer, the processor further configured to adjust the rhythmic component to the second target respiration rate responsive to the user maintaining the first target respiration rate for a maximum amount of time.

8. The apparatus of claim 1 wherein the processor is further configured to cause the transducer to provide entrainment cues including a rhythmic component associated with the target breath architecture.

9. The apparatus of claim 1 wherein the processor is further configured to play differing entrainment sounds over a number of sleep sessions, and to monitor how quickly the user falls asleep, and to determine one or more entrainment sounds that work well for causing the user to quickly fall asleep.

10. The apparatus of claim 1 wherein the processor is further configured to increase the target respiration rate, in response to the user being unable to match the target respiration rate within a certain period of time.

11. A method of encouraging relaxation in a user, the method comprising:
producing, by a transducer, entrainment cues having a rhythmic component at a target respiration rate;
detecting, by a biometric sensor, the user's respiration rate;
determining, by a processor coupled to the biometric sensor, whether the user's respiration rate meets a criterion, the criterion including a matching criterion that indicates the user's respiration rate matches the target respiration rate; and
gradually adjusting the entrainment cues, by the processor, responsive to the processor determining that the user's respiration rate has met the criterion for a defined amount of time, gradually adjusting the entrainment cues including lowering the target respiration rate.

12. The method of claim 11 wherein the criterion is a sleep criterion and adjusting the entrainment cues comprises ceasing the entrainment cues.

13. The method of claim 12 wherein determining whether the user's respiration rate meets the sleep criterion comprises determining that a variance of the user's respiration rate deviates from the target respiration rate by a threshold.

14. The method of claim 11 wherein the target respiration rate is within a range of five to nine respirations per minute.

15. The method of claim 11 further comprising limiting the target respiration rate to a lowest target respiration rate beyond which the target respiration rate is not lowered.

16. The method of claim 15 wherein the lowest target respiration rate is within a range of 5.5 respirations per minute to 6.5 respirations per minute.

17. An apparatus comprising:
a sensor configured to detect respiration of a user; and
a processor coupled to the sensor and having an output configured to be coupled to a loudspeaker and configured to:
cause the loudspeaker to play entrainment sounds having a rhythmic component at a first target respiration rate,
determine a respiration rate of the user, based at least in part upon the sensor, and
gradually adjust the rhythmic component to a second target respiration rate lower than the first target respiration rate responsive to determining that the user's respiration rate has matched the first target respiration rate for a defined amount of time.

18. The apparatus of claim 17 wherein the processor is further configured to determine that the user's respiration rate meets a sleep criterion and to cause the loudspeaker to cease playing entrainment sounds responsive to determining that the user's respiration rate meets the sleep criterion.

19. The apparatus of claim 18 wherein the processor is configured to detect that the user's respiration rate meets the sleep criterion based upon a variance of the user's respiration rate deviating from the target respiration rate by a threshold.

20. The apparatus of claim 17 wherein the processor is further configured to limit either of the first target respiration rate or the second target respiration rate to a lowest target respiration rate, the lowest target respiration rate being a target respiration rate beyond which the processor will not adjust the rhythmic component to be lower.

21. The apparatus of claim 20 wherein the lowest target respiration rate is within a range of 5.5 respirations per minute to 6.5 respirations per minute.

22. The apparatus of claim 17 wherein the processor is further configured to determine the defined amount of time based on how quickly the user's respiration rate matched the first target respiration rate.

* * * * *